United States Patent

Bonse et al.

[11] 4,456,769
[45] Jun. 26, 1984

[54] PREPARATION OF HYDRAZIDINES

[75] Inventors: Gerhard Bonse, Cologne; Thomas Schmidt, Haan, both of Fed. Rep. of Germany

[73] Assignee: Bayer Aktiengesellschaft, Leverkusen, Fed. Rep. of Germany

[21] Appl. No.: 387,906

[22] Filed: Jun. 14, 1982

[30] Foreign Application Priority Data

Jul. 9, 1981 [DE] Fed. Rep. of Germany ....... 3127042

[51] Int. Cl.³ .......................................... C07C 123/02
[52] U.S. Cl. .................................... 564/226; 564/250; 564/251
[58] Field of Search ........................ 564/226, 250, 251

[56] References Cited

PUBLICATIONS

Neilson et al., "The Chemistry of Amidrazones", *Chem. Rev.*, (1970), pp. 151–158.

*Primary Examiner*—Natalie Trousof
*Assistant Examiner*—L. Hendriksen
*Attorney, Agent, or Firm*—Sprung, Horn, Kramer & Woods

[57] ABSTRACT

A new one-step process for the preparation of hydrazidines of the general formula

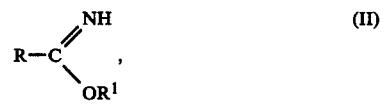

in which
R represents an optionally substituted alkyl group, an optionally substituted cycloalkyl group, an optionally substituted aryl group or an optionally substituted aralkyl group, or their acid addition salts, in high yield comprises reacting iminoalkyl ethers of the general formula $$R-C\begin{array}{c}\nearrow NH \\ \searrow OR^1\end{array} \quad (II)$$

in which
R has the abovementioned meaning and
$R^1$ represents an optionally substituted alkyl group or an optionally substituted cycloalkyl group, or their acid addition salts, with hydrazine in solvents under reduced pressure and at temperatures between $-80°$ and $+100°$ C., the reaction being effected in the presence of water present in the solvent and/or in the hydrazine by employing it as hydrazine hydrate. The hydrazidines of formula (I) and their salts are valuable intermediates in heterocyclic chemistry, for example for the synthesis of herbicidally active as-triazinones.

11 Claims, No Drawings

PREPARATION OF HYDRAZIDINES

The present invention relates to an unobvious process for the preparation of certain hydrazidines, most of which are known, starting from iminoalkyl ethers.

It is already known that acethydrazidine is obtained as the hydrochloride when, in a first step, acetiminoethyl ether hydrochloride is added to a previously prepared mixture of anhydrous hydrazine in absolute ethanol. After isolating the acetamidrazone hydrochloride thus formed in a yield of 50% of theory, this is reacted in a second step with anhydrous hydrazine dissolved in absolute ethanol to give acethydrazidine hydrochloride [see Mh. Chem. 63, 285–300 (1933)].

It is also already known that certain hydrazidines are obtained when imino ethers are initially converted into amidinium salts of carboxylic acids and these salts are converted with hydrazine into amidrazone salts; after the latter have been isolated, they are reacted, in a second step, with anhydrous hydrazine in an anhydrous solvent and the reaction mixture is then warmed for some time at 40° C. under reduced pressure (about 480 mbar) and, after removing the solvent, the corresponding hydrazidine salts are obtained (see Liebigs Ann. Chem. 749, pages 16–23 (1971) and Liebigs Ann. Chem. (1975), pages 1,120–1,123).

Acethydrazidine hydrochloride can thus be obtained, starting from acetamidine hydrochloride, in an overall yield of 83% of theory.

However, these multi-step processes have the disadvantage that, in addition to intermediate isolation of the amidrazone, further reaction with anhydrous hydrazine in anhydrous solvents is necessary. This implies a substantial technical expense; in addition, working with anhydrous hydrazine in the industrial synthesis represents a safety risk.

The present invention now provides a process for the production of a hydrazidine of the general formula

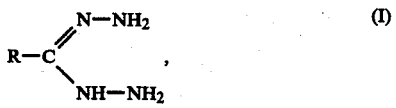

in which
R represents an optionally substituted alkyl group, an optionally substituted cycloalkyl group, an optionally substituted aryl group or optionally substituted aralkyl group, or an acid addition salt thereof, starting from a corresponding iminoalkyl ether, characterized in that an iminoalkyl ether of a carboxylic acid of the general formula

in which
R has the abovementioned meaning, and
$R^1$ represents an optionally substituted alkyl group or an optionally substituted cycloalkyl group, or an acid addition salt thereof, is reacted with hydrazine hydrate ($NH_2$-$NH_2 \times H_2O$) in a technical solvent (containing water) under reduced pressure and at a temperature between about −80° and +100° C. It is surprising that compounds of formula (I) and their salts can be obtained in very high yields and in a very pure form by the novel one-step procedure of the present invention.

The process according to the invention exhibits a number of advantages. In addition to substantially higher yields, it is particularly appropriate to carry out the entire reaction as a "one-pot process". In addition, hydrazine hydrate and technical solvents, i.e. solvents containing water, can be used instead of anhydrous hydrazine and absolute solvents.

Preferred hydrazidines of formula (I) which can be prepared by the process according to the present invention are those, in which R represents an optionally substituted, straight-chain or branched alkyl group with 1 to 12 carbon atoms, an optionally substituted cycloalkyl group with 3 to 6 carbon atoms, an optionally substituted aryl group with 6 or 10 carbon atoms or an optionally substituted aralkyl group with 6 or 10 carbon atoms in the aryl part and 1 to 4 carbon atoms in the alkyl part.

Suitable substituents on the previously mentioned optionally substituted groups of radical R are any of those substituents which do not react with hydrazine hydrate under the reaction conditions.

For example, the alkyl radicals of R can be substituted by halogen (particularly chlorine or fluorine) or by alkoxy or alkylthio with 1 to 4 carbon atoms in each case.

The cycloalkyl radicals of R can be substituted, for example, by halogen (particularly chlorine or fluorine), by alkyl, alkoxy or alkylthio with 1–4 carbon atoms in each case or by phenyl (which is itself optionally substituted).

The aryl and aralkyl radicals of R can be substituted, for example, by halogen (preferably fluorine, chlorine or bromine), by nitro, by alkyl, alkoxy or alkylthio with 1 to 4 carbon atoms in each case or by halogenoalkyl, halogenoalkoxy or halogenoalkylthio with 1 to 4 carbon atoms and up to 5 identical or different halogen atoms (particularly fluorine and chlorine atoms) in each case.

Particularly preferred compounds of the formula prepared by the process of the present invention are those in which R represents a methyl, chloromethyl, ethyl, n-propyl, isopropyl, n-butyl, sec.-butyl, tert.-butyl, cyclopropyl, cyclobutyl, cyclopentyl, cyclohexyl, phenyl or benzyl group.

If, for example, acetiminoethyl ether hydrochloride and hydrazine hydrate are used as starting materials, the course of the reaction according to the present invention is illustrated by the following equation:

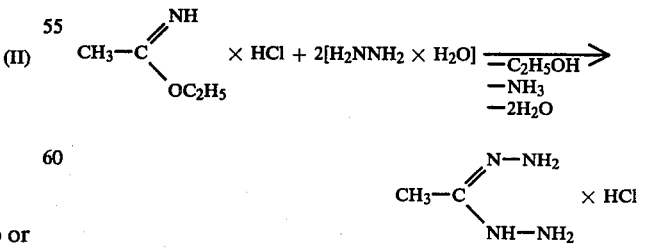

Preferred iminoalkyl ethers of formula (II) required as starting materials for carrying out the process according to the invention are those in which R represents those radicals which have already been mentioned, in connection with the description of the preferred compounds of the formula (I), and R¹ represents an optionally substituted, straight-chain or branched alkyl group with 1 to 12 carbon atoms or an optionally substituted cycloalkyl group with 3 to 6 carbon atoms.

Suitable substituents on the optionally substituted groups of radical R¹ are any of those substituents which do not react with hydrazine hydrate under the reaction conditions.

For example, the alkyl radicals of R¹ can be substituted by halogen (particularly chlorine or fluorine) or by alkoxy and alkylthio with 1 to 4 carbon atoms in each case.

The cycloalkyl radicals of R¹ can be substituted, for example, by halogen (particularly chlorine or fluorine), by alkyl, alkoxy or alkylthio with 1 to 4 carbon atoms in each case or by phenyl (which is itself optionally substituted).

Iminoalkyl ethers of the formula (II) and their acid addition salts are compounds generally known in organic chemistry, and they can be prepared by known processes (compare Org. Synthesis Coll. Vol. I, page 5 (1951); Beilstein Vo. 2, page 182, 2, page 245; 2/III, page 451; 2/III, page 618; 2/III, page 675).

Examples which may be mentioned are: acetiminoethyl ether, chloroacetiminoethyl ether, trichloroacetiminomethyl ether, trichloroacetiminoethyl ether, propioniminoethyl ether, butyriminoethyl ether, valeriminoethyl ether and their hydrochlorides, preferably acetiminoethyl ether hydrochloride.

Suitable diluents for the reaction according to the invention are inert organic solvents, which can all be in the form of technical solvents containing up to about 20% of water, e.g. about 0.1 to 20%.

These include, as preferences, alcohols (such as methanol, ethanol, n-propanol, isopropanol, n-butanol, isobutanol, tert.-butanol, glycol, glycerol, amyl alcohol, cyclohexanol, 2-methylpentan-4-ol, methylglycol, n-hexanol, isohexyl alcohol, isoheptyl alcohol, n-heptanol, nonyl alcohol, dodecyl alcohol or methylcyclohexanol), ethers (such as tetrahydrofuran, dioxane or ethylene glycol monomethyl ether), amides (such as dimethylformamide, diethylformamide, dimethylacetamide or N-methylpyrrolidone), hydrocarbons (such as benzene or toluene), and halogenated hydrocarbons (such as methylene chloride, chloroform, carbon tetrachloride, 1,2-dichloroethane, 1,1,2-trichloroethane, trichloroethylene and chlorobenzene). Appropriate mixtures of solvents can also be used.

The reaction is carried out under reduced pressure, in order to remove the ammonia liberated in the reaction from the reaction mixture. It is appropriate to work in the range of pressure from 0.1 to 800 mbar, preferably working at pressures between 50 and 300 mbar.

The reaction temperatures can be varied within a relatively wide range, and depend on the pressure employed in each case. The reaction can, as mentioned above, be carried out in the temperature range from −80° to +100° C., preferably working between −30° and +50° C. The process can be carried out continuously or discontinuously.

On carrying out the process according to the invention, 2 to 2.5 mols, preferably 2 to 2.3 mols, of hydrazine hydrate are generally employed per mol of the iminoalkyl ether of the formula (II) or its corresponding acid addition salt.

The isolation of the products from the process of the formula (I) is effected in the customary manner by removal of the solvent. The hydrazidines or acid addition salts of hydrazidines, which are produced by the process according to the invention in high yields and high purity, can preferably be reacted as a solution or suspension to give secondary products without being isolated.

Hydrazidines are valuable structural units for the synthesis of numerous heterocyclic compounds, in this case in particular for herbicidally active as-triazinones (compare Liebigs Ann. Chem. 1976, pages 2,206–2,221; ibid. 1975, pages 1,120–1,123; Chem. Ber. 108, pages 3,509–3,517 (1975); Chem. Ber. 112, pages 1,981–1,990 (1979); DE-OS (German Published Specification) 2,224,161; DE-OS (German Published Specification) 2,556,835; and U.S. Ser. No. 338,811, filed Jan. 11, 1982, now pending.

The following example merely illustrates the process of the present invention in more detail.

PREPARATIVE EXAMPLE

Example 1

Acethydrazidine hydrochloride

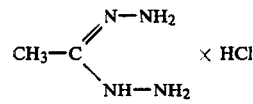

31.4 g (0.62 mol) of hydrazine hydrate in 200 ml of ethanol were put in a 1 liter three-necked flask, and the pressure was reduced to 100 mbar. A suspension of 38 g (0.31 mol) of acetiminoethyl ether hydrochloride in 200 ml of technical ethanol containing about 5% of water was then added with vigorous stirring, and stirring was continued for a further 2 hours. The ethanol was then removed in vacuo and, after drying, 36.9 g of acethydrazidine hydrochloride were obtained as colorless crystals, decomposition point 140°–150° C., of purity 90% (determined by polarography), with corresponded to a yield of 86% of theory.

Using the procedure described in Example 1 for the preparation of acethydrazidine, the compounds of the formula

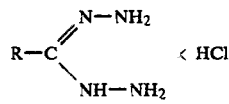

(I a)

listed in the following table could also be prepared:

TABLE

| Compound No. | R | Yield (% of theory) | Melting point (°C.) |
|---|---|---|---|
| 2 | C₂H₅ | 80 | 109–112 |
| 3 | n-C₃H₇ | 76 | 105–115 |
| 4 | iso-C₃H₇ | 71 | 126–128 |
| 5 | ClCH₂ | 78 | 135–138 |
| 6 | Cl₃C | 69 | 112–115 |

It will be understood that the specification and examples are illustrative but not limitative of the present invention and that other embodiments within the spirit and scope of the invention will suggest themselves to those skilled in the art.

We claim:

1. In the production of a hydrazidine of the formula

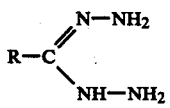

in which
R is an optionally substituted alkyl group, an optionally substituted cycloalkyl group, an optionally substituted aryl group or an optionally substituted aralkyl group,
or an acid addition salt thereof, by reacting the corresponding iminoalkyl ether of the formula

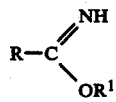

in which
$R^1$ is an optionally substituted alkyl group or an optionally substituted cycloalkyl group,
or an acid addition salt thereof, with hydrazine in a solvent, the improvement which comprises effecting the reaction using hydrazine hydrate in the presence of an inert organic solvent under reduced pressure and at a temperature between about $-80°$ and $+100°$ C.

2. A process according to claim 1, wherein the solvent contains about 0.1 to 20% of water.

3. A process according to claim 1, wherein the pressure ranges from about 0.1 to 800 mbar.

4. A process according to claim 1, wherein the temperature is between about $-30°$ and $+50°$ C.

5. A process according to claim 1, wherein about 2 to 2.5 mols of hydrazine hydrate are employed per mol of the iminoalkyl ether acid addition salt thereof.

6. A process according to claim 1, in which R is an optionally substituted alkyl group with 1 to 12 carbon atoms, an optionally substituted cycloalkyl group with 3 to 6 carbon atoms, an optionally substituted aryl group with 6 or 10 carbon atoms or an optionally substituted aralkyl group with 6 to 10 carbon atoms in the aryl part and 1 to 4 carbon atoms in the alkyl part.

7. A process according to claim 1, in which R is a methyl, chloromethyl, ethyl, n-propyl, isopropyl, n-butyl, sec.-butyl, tert.-butyl, cyclopropyl, cyclobutyl, cyclopentyl, cyclohexyl, phenyl or benzyl group.

8. A process according to claim 1, in which $R^1$ is an optionally substituted alkyl group with 1 to 12 carbon atoms or an optionally substituted cycloalkyl group with 3 to 6 carbon atoms.

9. A process according to claim 1, wherein the iminoalkyl ether is selected from the group consisting of acetiminoethyl ether, chloroacetimonoethyl ether, trichloroacetiminomethyl ether, trichloroacetiminoethyl ether, propioniminoethyl ether, butyriminoethyl ether, valeriminoethyl ether and the hydrochlorides thereof.

10. A process according to claim 1, wherein the reactants are acetiminoethyl ether hydrochloride and hydrazine hydrate.

11. A process according to claim 10, about 2 to 2.3 mols of hydrazine hydrate being employed per mol of iminoethyl ether, the solvent containing about 0.1 to 20% of water, the temperature ranging from about $-30°$ to $+50°$ C. and the pressure ranging from about 50 to 300 mbar.

* * * * *